United States Patent [19]

Jetten

[11] Patent Number: 5,420,033
[45] Date of Patent: May 30, 1995

[54] EPITHELIAL CELL LINE EXPRESSING A CYSTIC FIBROSIS PHENOTYPE

[75] Inventor: Anton M. Jetten, Durham, N.C.

[73] Assignee: The United States of America as represented by the Secretary of the Department of Health and Human Services, Washington, D.C.

[21] Appl. No.: 368,725

[22] Filed: Jun. 21, 1989

[51] Int. Cl.$^6$ .......................... C12Q 1/02; C12N 5/06; C12N 15/06
[52] U.S. Cl. ............................. 435/240.2; 435/240.1; 435/172.1; 435/172.3; 935/71; 935/70; 935/66
[58] Field of Search ...................... 435/5, 29, 6, 172.1, 435/172.3, 240.1, 240.2; 935/71, 70, 66

[56] References Cited

U.S. PATENT DOCUMENTS 5,100,647  3/1992  Agus et al. ............................... 424/45

OTHER PUBLICATIONS

Yankaskas et al, Am. Rev. Respir. Dis., vol. 143, Abstract A139, 1991.
Scholte, B. J., et al., Experimental Cell Research, vol. 182 (Jun. 1989) 559–571.
Gruenert, D. C., et al., Proc. Natl. Acad. Sci. USA, vol. 85 (Aug. 1988) 5951–5955.
Jetten, A. M., et al., Science, vol. 244, (23 Jun. 1989) 1472–1475.
Lu, L., et al., Biological Abstracts, vol. 89, No. 4, abstract No. 37371 (1990).
Buchanan, J. A., et al., Journal of Cell Science, vol. 95 (1990) 109–123.
P. L. Zeitlin, et al., A Cystic Fibrosis Bronchial Epithelial Cell Line: Immortalization by Adeno–12SV40 Infection. vol. 4. pp. 331–319, 1991.
Douglas M. Jefferson, et al., Expression of Normal and Cystic Fibrosis Phenotypes by Continuous Airway Epithelial Cell Lines. Am. J. Physiol. 259: L496–L505 (1990).

*Primary Examiner*—Toni R. Scheiner
*Attorney, Agent, or Firm*—Needles & Rosenberg

[57] ABSTRACT

An airway epithelial cell line (CF/T43) was developed by infecting cultured cystic fibrosis (CF) airway epithelial cells with the pZIPneoSV(X)1/SV40T retrovirus and selecting for Genetian (G418) resistance and ion transport properties. The distinctive chloride secretory phenotype of CF/T43 [an apical membrane chloride permeability ($P_{cl}-$) activated by calcium-mediated, but not by adenosine 3',5'-monophosphate (cAMP)-dependent agonists] was not perturbed by SV40T-induced cell transformation. Epithelial cell lines generated from CF cells with the SV40T gene can be used to test candidate CF genes, to evaluate the molecular mechanisms responsible for the CF phenotype and to test putative therapeutic CF drugs.

2 Claims, 8 Drawing Sheets

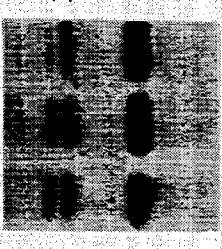

Change in $I_{eq}$ of Amiloride Pretreated Cell Lines

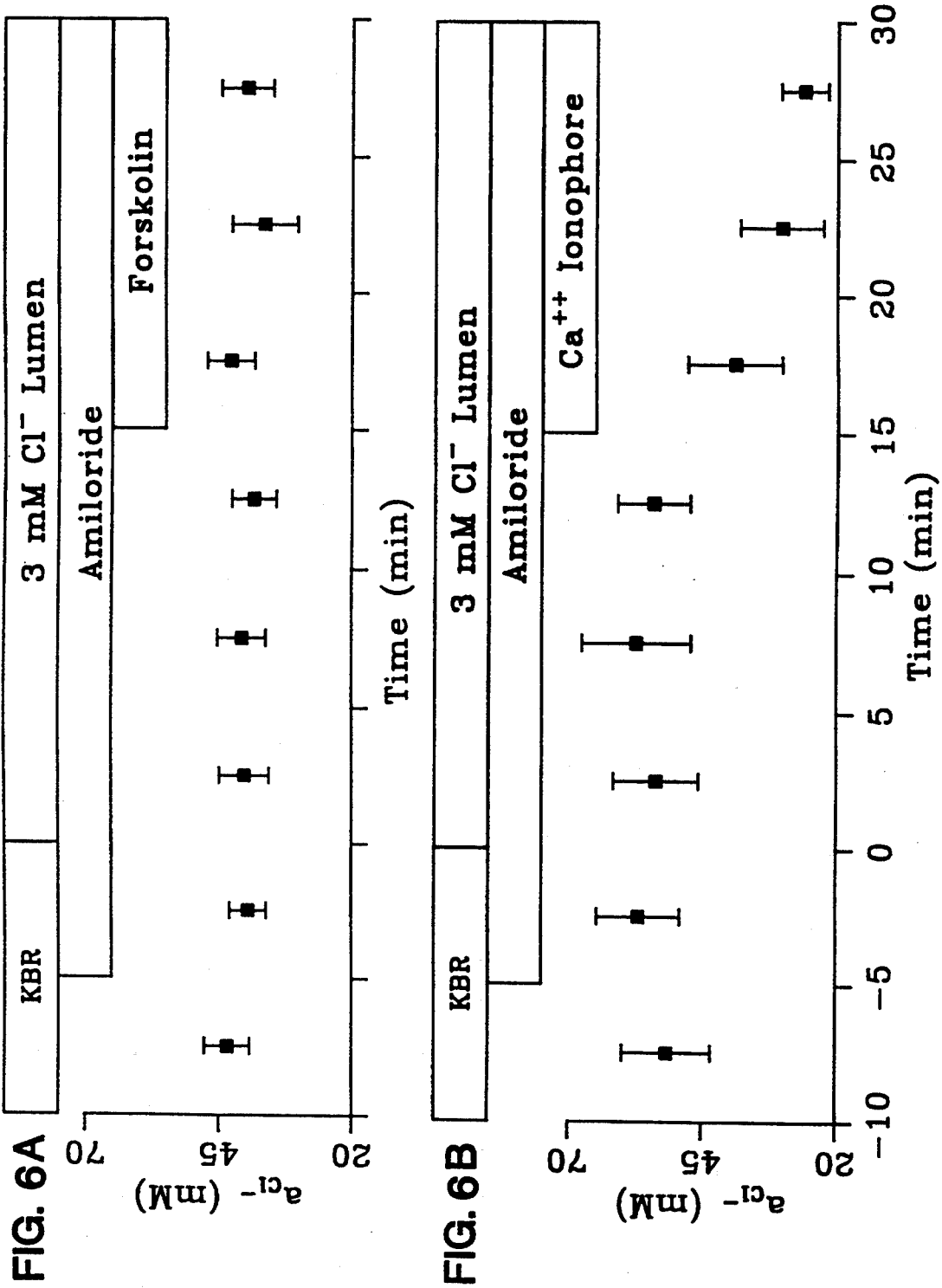

EPITHELIAL CELL LINE EXPRESSING A CYSTIC FIBROSIS PHENOTYPE

BACKGROUND OF THE INVENTION

The present invention relates to a transformed epithelial cell line that maintains the abnormal ion transport characteristics of cystic fibrosis while extending the proliferation capability beyond that of a primary epithelial cell culture. Moreover it relates to the testing of putative therapeutic compounds on such transformed cells as well as to applying genetic complementation analysis of candidate cystic fibrosis genes on such transformed cells.

Cystic fibrosis (CF) is an autosomal recessive disease that affects epithelia of the airways, sweat glands, pancreas, and other organs. Abnormal regulation of transport proteins in the apical cell membrane, including the conductive $Cl^-$ channel, is the direct effect of the abnormal gene.

There is a pressing need to develop treatments for CF. Based on what is presently known of the biochemical effects resulting from the genetic defect it may be possible to find compounds that are able to ameliorate the effects of the disease. In the case of many physiological defects therapeutic drugs have been identified using isolated cells for rapid mass screening of candidate drugs. Therefore it would be ideal to have such a screening system for CF.

CF abnormalities are exhibited in primary cultures of CF epithelial cells however the difficulties associated with obtaining tissue and with growing isolated cells from the tissue currently restricts the approach described above. A number of other human epithelial cell types have previously been transformed by SV40T genes in attempts to enhance the growth potential of the cell line including human bronchial epithelial cells (Reddel et al., Cancer Research 48, 1904–1909, 1988). The epithelial cell line of this invention with its expanded growth potential increases the availability of phenotypic cystic fibrosis cells making possible screening of putative therapeutic drugs and analysis of cystic fibrosis genes.

SUMMARY OF THE INVENTION

This invention has for its object to provide an epithelial cell line that has a cystic fibrosis ion transport phenotype. An additional object is to provide a greater source of cells that manifest the essential properties of cystic fibrosis. It is a further object to make available cells manifesting the cystic fibrosis phenotype on which to test genes suspected of containing a defect that causes the cystic fibrosis phenotype. Moreover the invention has as an object to provide the cells instrumental for developing and testing innovative therapeutic strategies.

Transformation by viral oncogenes and carcinogens has been reported to enhance the growth potential of cultured airway epithelial cells by Gruenert et al. published in August of 1988 (PNAS 85, 5951 (1988)). However, no attempts to transform CF epithelial cells has been reported. In addition under the conditions used the reported transformed epithelial cells failed to develop sufficient intercellular tight junctions. Since intercellular tight junctions are responsible for the transepithelial electrical resistance ($R_t$) an appreciable Rt also failed to be induced in the reported cultures.

The present invention relates to a cell line comprised of epithelial cells having an enhanced growth potential compared to primary cell cultures of the same cell type and expressing a cystic fibrosis ion transport phenotype.

The term "cell line" as used herein refers to a genetic lineage of cells derived from a primary culture by subculturing. According to common usage in the art, a primary culture is the initial culture of cells freshly isolated from a tissue. Although it is inherently impossible to establish that any cells truly have an unlimited lifespan in culture or, in the common terminology of the art, that they are "immortal", the present invention contemplates cultures with no practical limitation on growth potential.

In practice, the enhanced potential for growth of the cell line of this invention provides a greater number of progeny cells from a culture than would a primary culture of the same type of cells (i.e., cells taken from the same kind of tissue as the cells that originated the cell line). It will be appreciated by one of ordinary skill in the art, of course, that the extent to which cells replicate (i.e., the number of generations that the cells undergo) upon subculturing depends on various culture conditions including the density that the cells are seeded into each successive subculture. Nevertheless, the increased growth potential as expressed in terms of increased potential for subculturing will be recognized as a direct indication of the ability for a cell line ultimately to produce more prodigy than a primary cell culture.

In a principal embodiment of this invention, as described below (see Example 1), the growth potential of a line of epithelial cells was increased to at least about 16–19 subcultures, and preferably to at least about 30 subcultures without loss of viability or of the ability to express a cystic fibrosis ion transport phenotype. In contrast, primary cultures of the same cells that were not exposed to the SV40T gene can only be subcultured about four times before the cells senesce and cease proliferation (see Example 1, below).

The meaning of the phrase "transformed by an oncogene" as used herein indicates that an oncogene has been added to the genome of the cell and that the oncogene is expressed. It is well known in the art that a frequent consequence of such transformation is the enhancement of growth potential of the transformed cells. It will also be appreciated by one skilled in the art that transformation by an oncogene can be brought about by addition of an oncogene from an exogenous genetic source, including viral oncogenes (from either DNA viruses or retroviruses, for example) or mutant cellular homologs of viral oncogene genes. Further, such transformation may also result from generation of endogenous oncogenes from normal cellular genes by exposure of cells to carcinogenic agents, for example, to chemical carcinogens or radiation, or by spontaneous mutations. Accordingly, the present invention contemplates a cell line in which the cells are transformed by an oncogene as defined in any of the aforementioned mechanisms.

The meaning of the phrase "a cystic fibrosis ion transport phenotype" as used herein refers to a distinctive chloride ion secretion defect wherein apical membrane chloride ion permeability is activated by calcium-mediated but not by adenosine 3', 5'-monophosphate (cyclic-AMP) mediated agonists. This is in contrast to normal chloride ion transport which is responsive to both calcium-mediated and cyclic-AMP mediated agonists.

In the present embodiment, a cell line was derived from cells obtained from a donor with cystic fibrosis but the present invention allows for identical genetic defects brought about in cells not originating from a donor with cystic fibrosis. In turn, the invention allows for the creation of a cell line having a cystic fibrosis ion transport phenotype using genetic engineering methods. Accordingly, the present invention contemplates the creation of cells expressing cystic fibrosis derived from cells not obtained from a donor with cystic fibrosis.

While at present there is no known animal model system which manifests the cystic fibrosis ion transport phenotype and, therefore, the present embodiments relate to human cells, this invention also contemplates cells of other species that may be found in the future to be capable of developing cystic fibrosis.

Various other objects and advantages of the present invention will become obvious from the description of the invention when considered in connection with the accompanying drawings.

BRIEF DESCRIPTION OF THE DRAWINGS

FIG. 1 demonstrates the expression of the exogenous viral SV40T gene in a primary culture of normal airway epithelial cells (lane a), the transformed cystic fibrosis cell line CF/T43 (lane b), and the transformed normal airway epithelial cell line NL/T4 (lane c). Cells labeled with [$^{35}$S] methionine were lysised and immunoprecipitated with SV40T Ag monoclonal antibody. The precipitate was analyzed by polyacrylamide-SDS gel electrophoresis followed by autoradiography.

FIGS. 2A and 2B demonstrate the expression of AE1 cytokeratin and AE3 cytokeratin in a primary culture of normal airway epithelial cells (lane a), the transformed airway epithelial cell line CF/T43(lane b) and the transformed normal airway epithelial cell line NL/T4 (lane c). Proteins were separated from trypsinized cells by polyacrylamide gel electrophoresis, detected by immunoblotting and visualized by immunogold silver staining.

FIG. 6 shows the intracellular chloride activity ($a_{cl}-$) of amiloride pretreated transformed cystic fibrosis cells CF/T43 when exposed to forskolin, a cAMP-dependent agonist, or to a $Ca^{2+}$ ionophore.

DESCRIPTION OF SPECIFIC EMBODIMENTS

Figure 3A:
FIGS. 3a and 3b show grooves characteristic of tight functions in freeze fracture micrographs of CF/T43 cells (16,200×) (a) and in a primary culture of normal airway epithelial cells (20,800×) (b).

During the investigation which formed the basis of the present invention a epithelial cell line was derived from cystic fibrosis nasal epithelial cells which were transformed with the simian virus SV40T gene. Colonies resistant to neomycin were isolated and grown in conditions that induce the development of intercellular tight junctions and a transepithelial electrical resistance ($R_t$) in the transformed cultures. Clones were selected that formed resistive epithelial barriers and the regulation of their ion transport properties was characterized with intracellular microelectrodes and patch clamp techniques. The cell line, CF/T43, was obtained which expressed transformation and epithelial specific characteristics. In addition the epithelial cell line manifested the specific cystic fibrosis ion transport property an apical membrane chloride permeability that is activated by calcium-mediated but not by cyclic AMP mediated agonists.

The key features of the CF/T43 line, are the formation of functional tight junctions, reduced apical membrane chloride conductance $G_{cl-}$, and activation of apical Cl− channels by a $Ca^{2+}$ ionophores but not by cAMP-dependent agonists, indicating the cell line is functioning like epithelial cells that have a ion channel defect found in cystic fibrosis. These characteristics are essential in elucidating the mechanisms of CF, testing candidate complementary genes for correction of the observed CF abnormalities, and for developing and testing innovative therapeutic strategies.

The invention is further illustrated by the following examples describing the preferred methods. All publications mentioned hereunder are incorporated herein by reference.

EXAMPLE 1: CELL TRANSFORMATION

Primary cultures of airway epithelial cells were established from nasal polyps excised from a donor with CF. While in exponential growth phase, the cells were infected with a pZIPneoSV(X)1/SV40T retrovirus (Cepko et al., Am. J. Physiol.; Cell 37, 1053 (1984); Jat et al., Mol. Cell. Biol. 6, 1204 (1986)). After 10 to 14 days, colonies resistant to G418 (a neomycin analog which is toxic to mammalian cells, 50 µg/ml) were isolated, propagated for further study in plastic tissue culture flasks in serum-free keratinocyte growth medium (KGM) (Clonetics Corps, San Diego, Calif.) and aliquots cryopreserved. Of these resistant colonies only a few displayed the CF phenotype. Several cell lines were established, but most ceased proliferation after several passages. A CF (CF/T43) cell line continued growing through 30 passages, and was used for further studies. Control cultures not exposed to the retrovirus senesced and died within four passages.

EXAMPLE 2: PARAMETER CHARACTERIZATION a) To show SV40T antigen expression in the transformed cells the cells were metabolically labeled with [$^{35}$S] methionine (100 µCi/ml; >1000 mCi/mmol; Amersham) in methionine-free Ham's F12 medium for 1 hour. The labeled cells were washed in phosphate buffered saline (PBS) and solubilized in lysis buffer (154 mM NaCl, 10 mM Na$_2$HPO$_4$, pH 7.2, 1% Triton X-100, 0.5% deoxycholate, 1 mM NaF). The homogenate was centrifuged at 50,000 xg for 1 hour and the supernatant (>10$^7$ tricarboxylic acid-precipitable counts per minute) immunoprecipitated with SV40T Ag (Ab-2a) mouse monoclonal antibody 416 (Oncogene Science, Manhasset, N.Y.) according to the manufacturer's protocol (Harlow, et al. J. Virol. 39, 861 (1981); Jetten, et al. J. Invest. Dermatol. 92, 203 (1989)). Immunoprecipitated antigens were analyzed by 8% polyacrylamide-SDS gel electrophoresis followed by autoradiography (Laemmli, Nature 227, 680 (1970)). The transformed cystic fibrosis cell line was shown to express the SV40T antigen. (FIG. 1).

b) To detect expression of epithelial cell specific AE1 cytokeratin and AE3 cytokeratin cells were collected by trypsinization and solubilized in sample buffer (62.5 mM Tris-HCl, pH 6.8, 1% sodium dodecylsulfate, 2 mM phenylmethylsulfonylfluoride, 1 mM EDTA, 2.5 µg/ml leupeptin, 2.5 µg/ml aprotinin, 5% glycerol, 50 mM dithiothreitol and 0.001% bromophenol blue, pH 6.8). Proteins were separated by 8% polyacrylamide gel electrophoresis (Laemmli, Nature 227, 680 (1970)). Immunoblot analysis performed. The reactivity of keratins with monoclonal antibodies AE1 and AE3 (Woodcock-Mitchell et al., J. Cell Biol. 95, 580 (1982)) was visualized by immunogold silver staining with Auro Probe BL plus streptovidin (Janssen Biotech, Olen, Belgium) according to the manufacturer's protocol. The continued epithelial nature of the SV40T transformed cells was confirmed with the expression of the AE1 cytokeratin and AE3 cytokeratin as seen in FIG. 2.

EXAMPLE 3: TIGHT JUNCTION AND $R_t$ INDUCEMENT

Transformed cell lines propagating in the plastic tissue culture flasks were then passaged to permeable collagen matrix supports (CMS), the medium was supplemented with factors that induce differentiation in other cultured cells [1.0 mM Ca$^{2+}$, 10$^{-9}$M retinoic acid and 50% Dulbecco's Modified Eagle medium (with 2% FBS) conditioned by NIH 3T3 fibroblasts (CM) (Yankaskas, et al., Am. Rev. Respir. Dis. 132, 1281 (1985); Vega-Salas et al., J. Cell Biol. 104, 905 (1987); Jetten et al. Lab. Invest. 56, 654 (1987); Ke et al., Differentiation 38, 60 (1988)) and $R_t$ was measured serially in a sterile modified Ussing chamber. Lines developing significant $R_t$s were evaluated by electrophysiological methods that distinguish normal and CF airway epithelial cells in primary culture (Boucher et al., Physiol. 405, 77 (1988); Willumsen et al., Am. J. Physiol. (Cell Physiol. 25) 256, C226 (1989); Willumsen et al., Am. J. Physiol. (Cell Physiol. 25) 256, C1045 (1989); Willumsen et al., Am. J. Physiol. (Cell Physiol. 25) 256, C1033 (1989)).

Figure 3B:

CF/T43 cells (passages 9 to 19) developed significant $R_t$s and equivalent short circuit current ($I_{eq}$). The $R_t$ of the cell lines was lower than that of primary cultures, while the transepithelial potential ($V_t$) and $I_{eq}$ were intermediate between the values reported by different investigators. The accompanying formation of morphologic correlates of tight junctions comparable to those of airway epithelial cells in primary culture were visualized in freeze fracture micrographs. CMS cultures were fixed in a mixture of phosphate-buffered 2% glutaraldehyde and 2% paraformaldehyde (pH 7.2). Prior to freezing, the samples were cryoprotected for 1 hour in a solution of 25% glycerol in 0.1M phosphate buffer. Samples were positioned on gold double-replica specimen mounts and frozen in liquid nitrogen. The samples were processed in a Balzers BAF400T freeze fracture apparatus (Balzers Corporation, Nashua, N.H.) at a stage temperature of −100° C. After fracturing, the specimens were shadowed with platinum-carbon and stabilized by evaporation. The replicas were cleaned in 5% sodium dichromate in 50% H$_2$SO$_4$ and retrieved from distilled water on copper grids. Replicas were viewed and photographed with a Zeiss EM-10A transmission electron microscope at an accelerating voltage of 60 kV, (Carson et al., Am. J. Anatomy 173, 257 (1985)). The results, FIG. 3, showed tight junctions, which preserve ion transport functions in cell cultures, had been formed in the transformed cell line culture.

EXAMPLE 4: ASSESSMENT OF BASAL CL$^-$ CONDUCTANCE ($G_{cl-}$)

Figure 4:
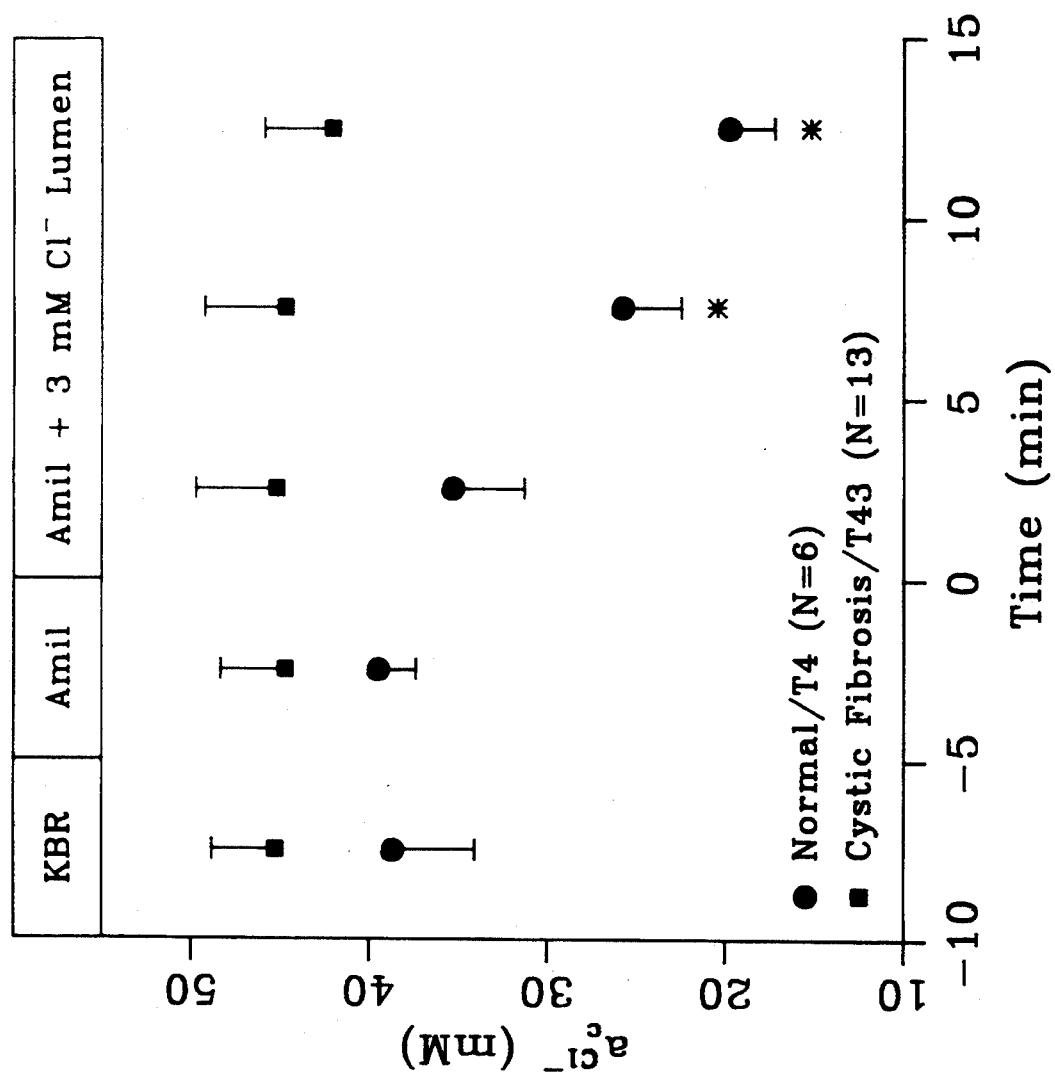
FIG. 4 shows the intracellular chloride activity ($a_{cl}-$) of amiloride pretreated transformed normal epithelial cells N/T4 and transformed cystic fibrosis epithelial cells CF/T43 in response to a large chemical gradient for Cl− exit.

CMS cultures were sequentially exposed to Krebs Bicarbonate Ringer (KBR) solution, amiloride (10$^{-4}$M, luminal) in KBR, and amiloride in 3 mM Cl$^-$ (Cl$^-$ replaced by gluconate) luminal solutions. Linear regression analyses to calculate the rate of change in intracellular Cl$^-$ activity ($a_{cl-}$) during 3 mM Cl$^-$ exposure and t-tests to estimate whether these rates differed from zero indicated that $a_{cl-}$ of CF/T43 did not change (−0.17±0.09 mM/min, n=13). Intracellular Cl$^-$ activity was measured with ionselective microelectrodes (Willumsen et al., Am. J. Physiol. (Cell Physiol. 25) 256, C1045 (1989)). Three to 10 impalements for each condition were averaged for each of 13 (CF/T43) cultures (FIG. 4). The results demonstrated that the transformed cystic fibrosis cells behaved as primary cultures of cystic fibrosis epithelial cells in regards to $a_{cl-}$ and that a negligible apical membrane $G_{cl-}$ conductance existed in the cells.

EXAMPLE 5: REGULATION OF APICAL MEMBRANE $G_{cl-}$

Figure 5:
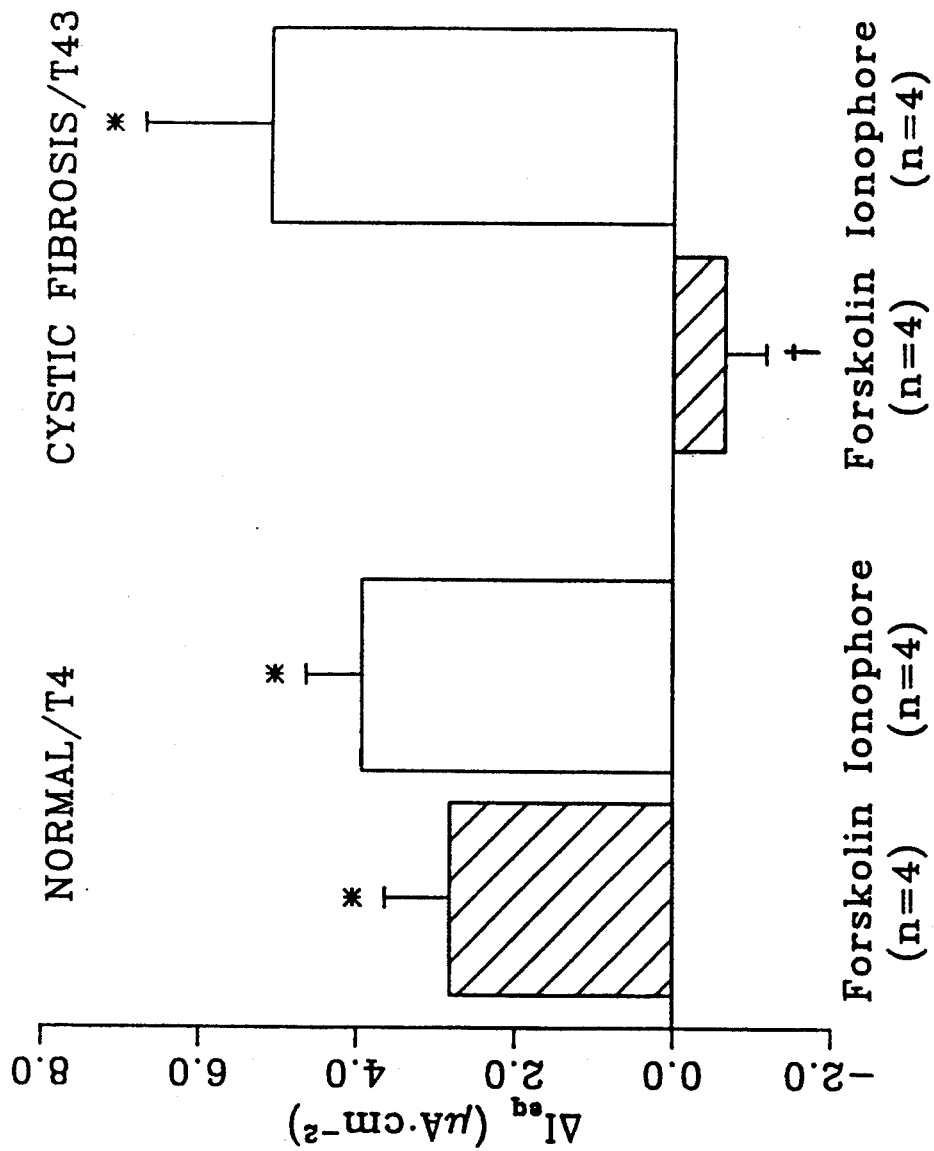
FIG. 5 shows charges in the equivalent short circuit current ($I_{eq}$) of amiloride pretreated transformed normal epithelial cells N/T4 and transformed cystic fibrosis epithelial cells CF/T43 when exposed to forskolin, a cAMP-dependent agonist or a $Ca^{2+}$ ionophore.

The following approaches were employed to evaluate the regulation of apical membrane $G_{cl-}$ in the transformed cystic fibrosis CF/T43 cell line.

a) CMS cultures were pretreated with amiloride (10$^{-4}$M) and then exposed to forskolin (10$^{-5}$M, luminal) a cAMP-dependent agonist, or a Ca$^{2+}$ ionophore (A23187, 10$^{-6}$M, or ionomycin, 10$^{-5}$M, luminal). The equivalent short circuit current ($I_{eq}$) was measured before and after secretogogue exposure to determine the capability of forskolin and the Ca$^{2+}$ ionophore to increase the $I_{eq}$. The Ca$^{2+}$ ionophores were effective as Cl$^-$ secretogoues in the CF/T43 cell line while forskolin caused no response in the $I_{eq}$. (FIG. 5).

Figure 7A:
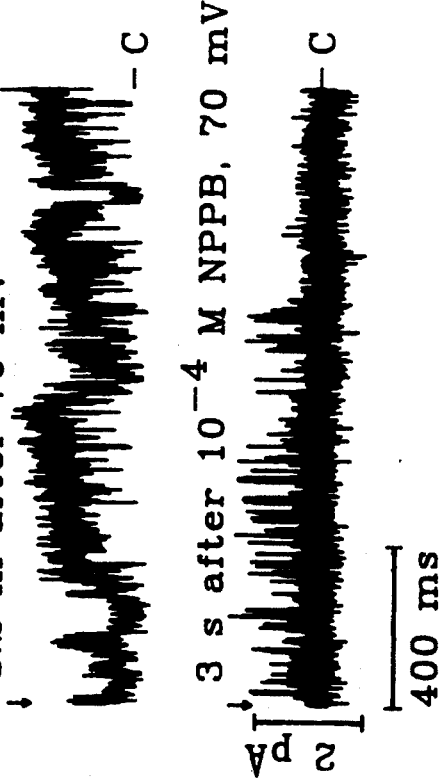
FIG. 7A shows activation response of Cl− channels in inside out patches from transformed normal epithelial cells to adenosine triphosphate (ATP), ATP plus catalytic subunit (CS) of cAMP-dependent kinase, and to Cl− channel blocker 5-nitro-2-(3-phenylpropylamino)- benzoic acid (NPPB).
Figure 7B:
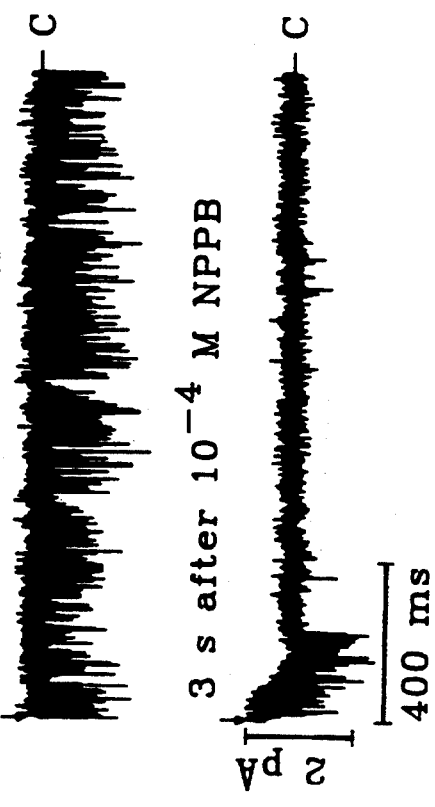
FIG. 7B shows activation response of Cl− channels in inside out patches from transformed cystic fibrosis epithelial cells CF/T43 to adenosine triphosphate (ATP), ATP plus catalytic subunit (CS) of cAMP-dependent kinase, and to Cl− channel blocker 5-nitro-2-(3-phenylpropylamino)- benzoic acid (NPPB).
Figure 7C:
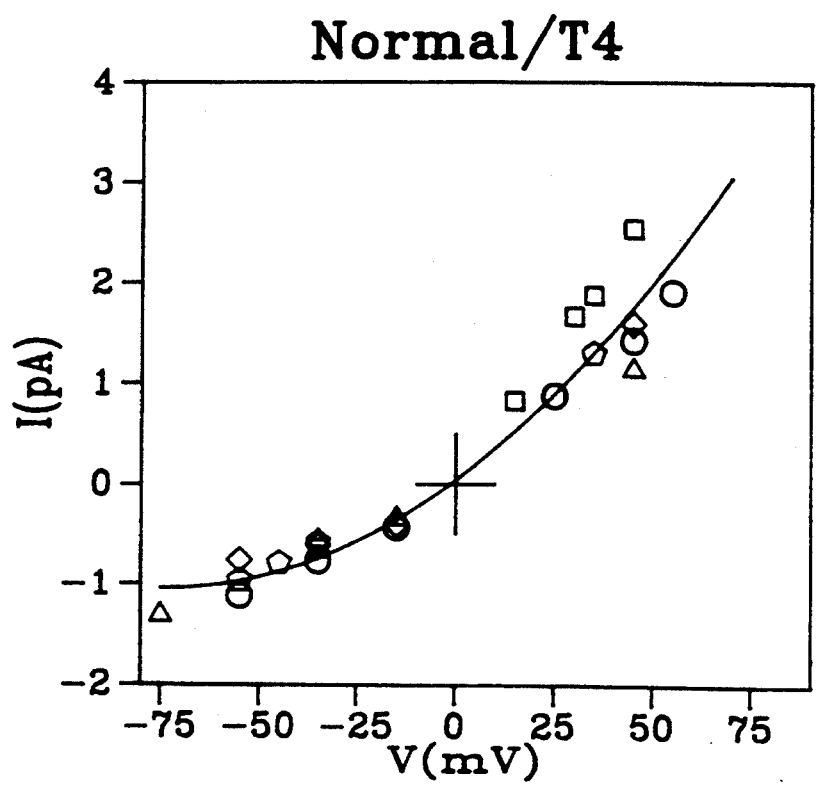
FIG. 7C shows current voltage relationship of Cl− channels from transformed normal epithelial cells.
Figure 7E:
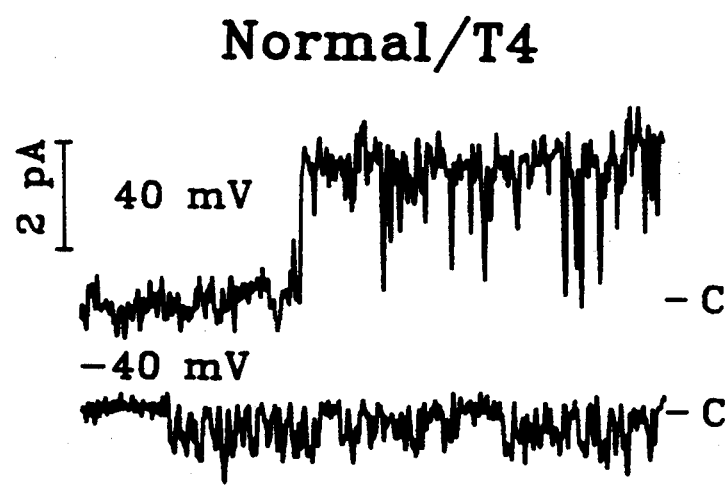
FIG. 7E shows recordings of transformed normal epithelial cells which demonstrate increased conductance at +40 mV clamp potential.
Figure 7D:
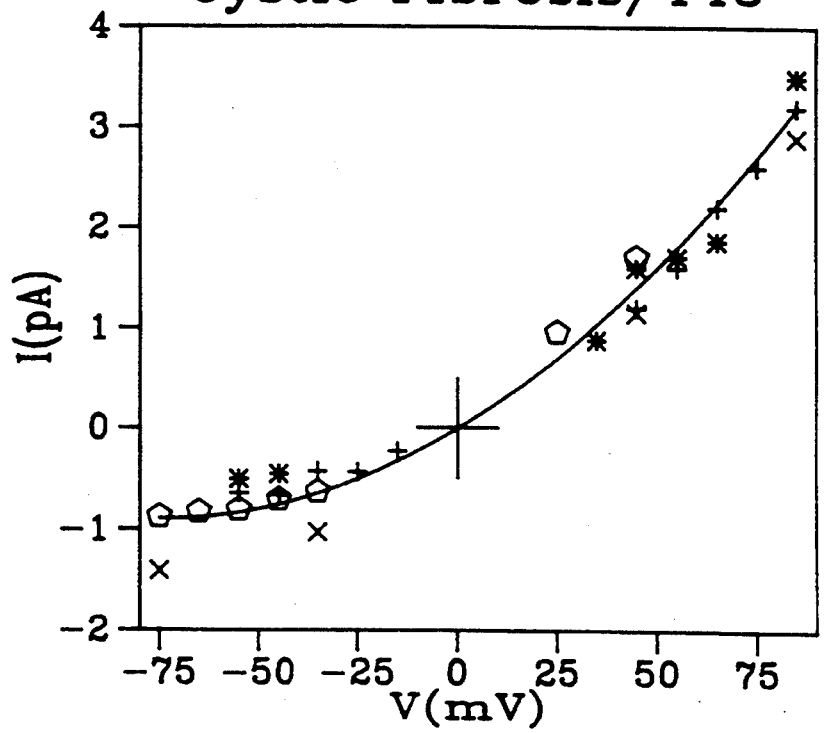
FIG. 7D shows current voltage relationship of Cl− channels from transformed cystic fibrosis epithelial cells CF/T43.
Figure 7F:
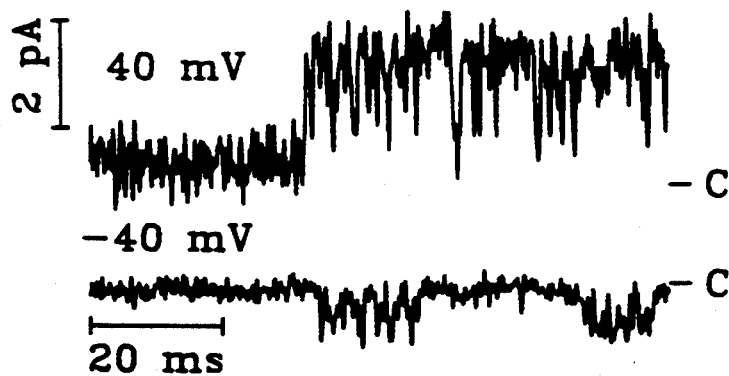
FIG. 7F shows recordings of transformed cystic fibrosis epithelial cells CF/T43 which demonstrate increased conductance at +40 mV clamp potential.

The lack of CF/T43 response to forskolin was not due to abnormal cAMP accumulation because forskolin increased cAMP levels (Steiner et al., J. Biol. Chem. 247, 1106 (1972)), comparably in CF/T43 (from 0.75±0.02 to 7.8±3.0 pM/mg protein, n=3) and a transformed normal epithelial cell line, NL/T4, (from 1.0±0.3 to 6.1±0.9 pM/mg protein, n=3) cells.

b) To further assess whether $Ca^{2+}$ ionophores increased apical $G_{cl-}$ in the cystic fibrosis transformed cells, the effects of ionomycin (n=1) and A23187 (n=3) with forskolin in amiloride pretreated cultures that were exposed to reduced (3 mM) luminal $Cl^-$ were compared. Cultures were sequentially exposed to KBR, amiloride in KBR, and amiloride in 3 nM $Cl^-$ luminal solutions, then exposed to forskolin ($10^{-5}$M, luminal) or a $Ca^{2+}$ ionophore (A23187, $10^{-6}$M, or ionomycin, $10^{-5}$M, luminal) in amiloride, 3 mM $Cl^-$ solution. $a_{cl-}$ did not change (−0.04±0.31 mM/min, n=6) during forskolin exposure, but decreased significantly (−1.85±−0.26 mM/min, n=4, p<0.01) during ionophore exposure. Calcium ionophores, but not forskolin, induced a decrease in $a_{cl-}$ (FIG. 6), reflecting a $Ca^{2+}$ mediated activation of an apical membrane $G_{cl-}$.

c) $Cl^-$ channel regulation at the single channel level was assessed. Schoumacher et al., Nature 330, 752 (1987); and Li et al., Nature 311, 358 (1988); found that the catalytic subunit (CS) of cAMP-dependent kinase activated outwardly rectifying $Cl^-$ channels in excised patches of normal but not CF airway epithelial cells. Excised inside-out patches were formed by the method of Hamill et al., (Pfluegers Arch. 391, 85 (1981)). The pipet solution was 140 mM NaCl, 2 mM $MgCl_2$, 1 mM ethylene glycol bis-(beta-aminoethyl ether) N,N,N′,N′-tetraacetic acid, 0.71 mM $CaCl_2$ and 5 mM TES (pH 7.2). The cytoplasmic face of the membrane was first exposed to bath solution containing 1 mM ATP. After 5 min the bath was changed to one which contained 1 mM ATP and 100 nM CS. If no activation occurred after 8 to 10 minutes, the patch voltage was depolarized to 70 to 100 mV. After activation, channels were identified by conductance, kinetics, reversal potential in symmetric pipet:bath solutions, outward rectification (Schoumacher et al., Nature 330, 752 (1987); Li et al., Nature 311, 358 (1988)), and by sensitivity to NPPB. All patch clamp experiments were performed at 20° to 22° C. 5 out of 16 inside-out patches taken from the transformed cells were found to contain $Cl^-$ channels. None of these were activated by the ATP or ATP plus CS (FIGS. 7A, B); all were activated by depolarizing voltages (FIGS. 7C, D). Chloride channels from CF/T43 had conductances [28.7±1.3 pS (n=5)] (FIGS. 7E, F) similar to those reported for CF airway epithelial cells in primary culture (Schoumacher et al., Nature 330, 752 (1987); Li et al., Nature 311, 358 (1988)).

We claim:

1. An immortalized cell line comprising epithelial cells expressing a cystic fibrosis ion transport phenotype, wherein said cells form tight junctions in culture and are transformed by SV40T.

2. The cell line according to claim 1, said cell line being the CF/T43 cell line.

* * * * *

UNITED STATES PATENT AND TRADEMARK OFFICE
CERTIFICATE OF CORRECTION

PATENT NO. : 5,420,033
DATED : May 30, 1995
INVENTOR(S) : Anton M. Jetten, Durham, N.C.; James R. Yankaskas, Chapel Hill, N.C.

It is certified that error appears in the above-indentified patent and that said Letters Patent is hereby corrected as shown below:

On the title page, item [75]:inventor, which reads "Anton M. Jetten, Durham, N.C.", should read -- Anton M. Jetten, Durham, N.C.; James R. Yankaskas, Chapel Hill, N.C. --

Signed and Sealed this

Sixteenth Day of July, 1996

Attest:

BRUCE LEHMAN

*Attesting Officer*     *Commissioner of Patents and Trademarks*